United States Patent [19]
Fischer et al.

[11] Patent Number: 5,738,869
[45] Date of Patent: Apr. 14, 1998

[54] TRANSDERMAL DRUG PREPARATION

[75] Inventors: Wilfried Fischer; Thomas Struengmann, both of Holzkirchen, Germany

[73] Assignee: Haxal AG, Holzkirchen, Germany

[21] Appl. No.: 535,035
[22] PCT Filed: Apr. 22, 1994
[86] PCT No.: PCT/EP94/01259
  § 371 Date: Jan. 16, 1996
  § 102(e) Date: Jan. 16, 1996
[87] PCT Pub. No.: WO94/25069
  PCT Pub. Date: Nov. 10, 1994

[30] Foreign Application Priority Data

Apr. 23, 1993 [DE] Germany ............... 43 13 402.5

[51] Int. Cl.$^6$ ............... A61K 9/127; A61K 9/06; A61K 9/10
[52] U.S. Cl. ............... 424/450; 424/405; 424/45
[58] Field of Search ............... 424/450, 405, 424/45; 514/56

[56] References Cited

U.S. PATENT DOCUMENTS

| | | | |
|---|---|---|---|
| 4,239,754 | 12/1980 | Sache et al. | 424/183 |
| 4,711,906 | 12/1987 | von Stetten | 514/516 |
| 4,745,105 | 5/1988 | Griffin et al. | 536/21 |
| 4,745,107 | 5/1988 | Foley et al. | 514/56 |
| 5,482,965 | 1/1996 | Rajadhyaksha | 514/452 |
| 5,498,420 | 3/1996 | Edgar et al. | 424/450 |

Primary Examiner—Thurman K. Page
Assistant Examiner—Murthy Sikha
Attorney, Agent, or Firm—Burgess, Ryan & Wayn

[57] ABSTRACT

The invention concerns a transdermal active-substance combination containing phospholipid, alcohol and vitamin E.

7 Claims, 3 Drawing Sheets

Skin permeation profile in vitro for a diethylammonium diclofenac emulsion gel (3 determinations)

Skin permeation profile in vitro for a diclofenac gel according to the invention (3 determinations)

TRANSDERMAL DRUG PREPARATION

BACKGROUND OF THE INVENTION

1. Field of the Invention

This invention relates to a transdermal drug combination containing phospholipid, alcohol and vitamin E.

2. Prior Art

The transdermal administration of drugs, for example anti-inflammatory or antithrombotic drugs, is appropriate in cases in which a high local concentration of the drugs in the tissue under the intact skin is necessary, while oral or parenteral systemic administration leads to undesirable systemic side effects or it is not possible for this type of administration to offer the local concentration necessary. Drugs such as heparin sodium are in general employed topically in high concentrations because of low skin permeability. The intestinal absorption of this drug is negligible. Systemic effects are undesirable in the case of peripheral injuries. Many topical drug formulations may sensitize, dry out or even damage the skin where they are applied. Water-containing creams or ointments, which are often intended to avoid some of these undesirable side effects, must contain microbiological preservatives which for their part often lead to skin sensitization. There is therefore a need for safer, non-irritant absorption accelerators which additionally protect the skin and which, for drugs having a low skin permeation ability, are advantageous for increasing the drug concentration in the target tissue. Diclofenac sodium is an example of a non-steroidal anti-inflammatory drug (NSAID) which is employed extremely often, specifically in view of its problem-free and well-established clinical efficacy. In order to decrease the known local mucosal irritations after oral administration, topical administration forms are desirable for chronic use in the case of regional rheumatic symptoms. Metabolism in the first passage after oral administration, which occurs in the liver and leads to partial inactivation, can also be avoided by topical administration. In the following exposition, diclofenac was selected as an example of drugs having a low skin permeation ability.

The efficacy of topical diclofenac sodium preparations depends greatly on the capacity of the preparation to allow the drug to penetrate the intact skin. In particular, the horny layer represents a barrier for any drug permeation of the skin and penetration into the underlying inflamed tissue. Since the permeability of intact skin for diclofenac sodium is low, various experiments have been undertaken to increase skin permeation by use of various salts. IL-A-62 160 describes amine salts of diclofenac for increased skin penetration. DE-A-3 336 047 (=GB-A-2 128 087) describes a topical preparation based on an oil-in-water emulsion, which contains the diethylammonium salt of diclofenac. This salt is more lipophilic than the sodium salt and can permeate the skin at a higher rate. The use of this salt, however, is not without risk. It is known that secondary amines form highly carcinogenic nitrosamines. The preparation additionally contains diethylamine as a neutralizing agent for acrylic acid, which acts as a gel-forming agent for the gel preparation. Since secondary amines have these potential side effects, the German authorities responsible for registration (BGA) have recommended the replacement of these amines in cosmetic and pharmaceutical preparations. EP-A-0 372 527 describes the use of a hydroxyethylpyrrolidine salt of diclofenac having a higher water solubility than in the case of the sodium salt. This salt was combined with various absorption promoters, for example ethoxylated glycerides, lanolin esters or lecithin. Only in combination with these new salts were the absorption promoters able to accelerate the absorption to such an extent as the diethylamine salt. For this, compare Clin. Tri. J., 26 (1989) 304–309 (Galzigna et al.: percutaneous absorption of diclofenac after topical application, two different gel formulations). JP-A-02.049 722 describes the use of ammonia as a neutralizing agent for polyacrylic acid gels containing diclofenac sodium. If, as a neutralizing agent, not ammonia, but an alkylamine, for example monoethylamine, was taken, the skin permeation in vitro fell from 44.8 to 1.7%. EP-A-0 498 011 describes rubidium or caesium salts of diclofenac having a higher skin permeation in vitro than in the case of the sodium salt. The use of these salts, however, is critical, since both ions display their own pharmacological effects. Antidepressant effects thus occur, and, in particular, caesium increases the cerebral concentrations of serotonin and tryptophan. Its very long elimination half-life (50 to 100 days) can lead to accumulation in the body after chronic administration. Rubidium likewise has a long elimination half-life (40 days) and leads to a long-term accumulation. In some cases, it can increase central nervous activity and aggressiveness. EP-A-0 245 126 describes the calcium salt of diclofenac in combination with toxicologically hazardous absorption promoters, such as DMSO and azones. Besides the use of novel salts of diclofenac, various preparations containing synthetic absorption promoters have been developed. JP-A-01.013 020 thus describes diclofenac sodium emulsions, which contain dialkyl carboxylates and fatty acids, for topical use. A protective agent is additionally added in order to reduce microbiological contamination. According to WO-A-88/04 938, heterocyclic penetration accelerators, such as imidazolines or oxazolines, are employed for topical pharmaceuticals comprising diclofenac. The disadvantages of such accelerators, however, are their possible skin irritation and sensitizations. U.S. Pat. No. 4,670,254 describes diclofenac sodium gels which contain a high amount of ethanol and propylene glycol. Ethanol is a known absorption promoter for various drugs. Ethanol and propylene glycol are solvents for lipids and have the disadvantage that they dry out the skin. JP-A-60.146 823 uses nicotinates as absorption accelerators. As drugs, they lead to increased circulation and increased blood flow and thus accelerate transport from the administration site. They lead to hot sensations and disturbing side effects. EP-A-0 147 476 uses glycols and salicylates or peppermint oil or menthol as absorption accelerators. These substances, however, can cause skin irritations, and peppermint oil or menthol can lead to burning or to sensitization of the skin.

It is also known that phospholipids can increase the moisture content of the skin and the permeation of drugs through the skin. The literature reports for diclofenac sodium, however, are contradictory. According to Chem. Pharm. Bull., 35 (1987) 3807–3812 (Nishihata et al.) the permeation in vitro through rat skin increases if diclofenac is employed in an aqueous gel containing hydrogenated soya bean phospholipids (30% phosphatidylcholine and 70% phosphatidylethanolamine; iodine value about 6%). The amount permeated after 7 h was 5 times higher in the case of the gel containing 0.5% hydrogenated phospholipids than in solution without phospholipids. The drug concentration was 1.25% in each experiment. On the other hand, according to 2nd Liposome Research Days, N. L. Leiden, June 1992, page 5 (Enghausen & Müller-Goymann), phospholipids should show no accelerating effect in vitro even when an isolated stratum corneum was pretreated with phospholipids. This last-mentioned result agrees with observations of the inventors (Comparison Example 1).

SUMMARY OF THE INVENTION

The invention is based on the object of improving the permeation ability of transdermal drug preparations containing phospholipids.

According to the invention, it was surprisingly found that in the case of such transdermal drug preparations the permeation ability can be advantageously improved by the addition of vitamin E (α-tocopherol) or by addition of vitamin E derivatives. Embodiments of the invention are covered by the subject-matter of the patent claims.

DETAILED DESCRIPTION OF THE PREFERRED EMBODIMENTS

The combination of phospholipids with tocopherol or tocopherol derivatives and short-chain aliphatic alcohols leads to an unexpectedly high skin permeation in the case of drugs having a low permeation ability. Examples of such drugs are non-steroidal anti-inflammatory, antithrombotic, analgesic, anaesthetic, antibiotic, hormonal and antiallergic drugs. The drug preparations can be topical solutions, foes, sprays, gels, pastes, ointments, emulsions and liposomal dispersions. Since in the case of low alcohol concentrations an antimicrobial activity is produced, the use of additional preservatives is not necessary. Since, according to the invention, tocopherol or a tocopherol derivative is provided, further antioxidants are not necessary.

Drug preparations of the composition according to the invention are safe, non-toxic, well tolerable and have a skin protectant action which can be attributed to tocopherol or tocopherol derivatives. Reference may be made to the cosmetic preparations which are used widely and which are intended to prevent exogenous skin damage, for example due to UV irradiation. The preparations according to the invention are superior in comparison with known topical drug preparations, since absorption promoters or, under certain circumstances, not unhazardous salts are avoided, which can lead to skin irritation or even to skin damage.

It emerges from the following experimental data that the addition of vitamin E (α-tocopherol) or one of its derivatives surprisingly raises the permeation drastically above the value applying for a diethylammonium diclofenac gel. Values of up to approximately 4000 μg of drug/2.5 cm$^2$ could thus be determined (Table 1).

The invention is illustrated in greater detail below with the aid of examples and figures.

COMPARISON EXAMPLE 1

(Diethylammonium diclofenac)

Figure 1:
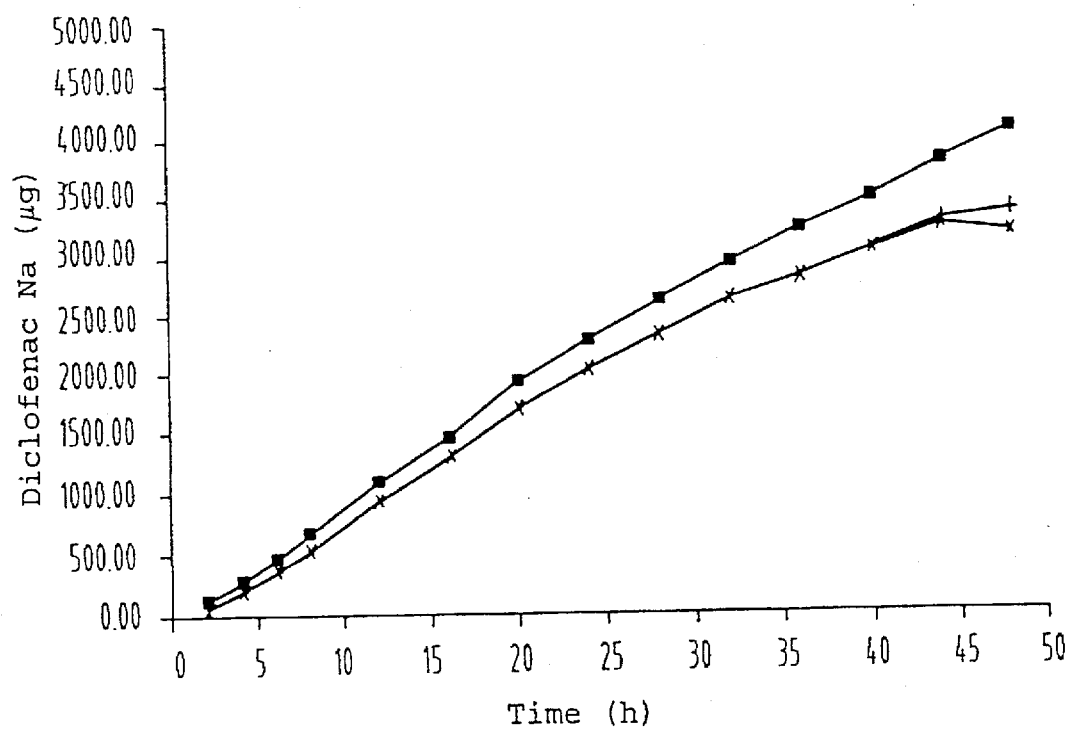
FIG. 1 shows a skin permeation profile in vitro of a diclofenac sodium gel of the prior art.

Skin permeation studies were carried out, dissected skin of nude mice being used in modified Franz cells. The permeation area was 2.5 cm$^2$. The acceptor medium was physiological saline solution at 34° C. A typical skin permeation profile is shown in FIG. 1. A commercially available emulgel (Voltaren) was used as a reference. It contains the diethylammonium salt of diclofenac. All amounts which permeated were expressed on the basis of diclofenac sodium. From this experiment it was possible to calculate an approximate flow rate of J=36 μg of drug/cm$^2$/h. The diethylammonium diclofenac gel had a permeation of approximately 2000 μg of drug/2.5 cm$^2$/24 h.

COMPARISON EXAMPLE 2

(Diclofenac sodium)

The skin permeation of saturated aqueous solutions and 1 per cent solutions was measured for a mixture of isopropanol and propylene glycol. The results can be seen in Table 1 below. The amount of drug which permeated through the skin in vitro in 24 hours in the case of a saturated and aqueous solution was thus 984 μg of drug/2.5 cm$^2$. This solution had maximum thermodynamic activity. A 1 per cent aqueous solution containing isopropyl alcohol and propylene glycol had a much lower permeation of 135 μg of drug/2.5 cm$^2$. The addition of 2% purified natural soya bean lecithin (about 80% phosphatidylcholine, 2% lysophosphatidylcholine, 4% phosphatidic acid and 1% monophosphatidylinositol) increased the permeation rate by a factor of approximately 5 to 750 μg of drug/2.5 cm$^2$, which approximately corresponded to the value of a saturated solution without absorption promoter. Phospholipids without addition of the alcohols led to a lower value of 230 μg of drug/2.5 cm$^2$.

TABLE 1

| Amounts of diclofenac sodium (μg/2.5 cm$^2$) which diffused in 24 h in various solvents | | | | |
|---|---|---|---|---|
| saturated aqueous solution | 1 per cent aqueous solution | 1% in IPA/PG water | 1% in water containing 2% PL | 1% in IPA/PG water + 2% PL |
| 984 | 398 | 150 | 230 | 750 |

IPA: Isopropyl alcohol
PG: Propylene glycol
PL: Phospholipid (as indicated above)

Since the solubility in water is approximately 1.9%, the values for skin permeation for solutions in water agree with the concentration differences. The 1:1 mixture of isopropanol (IPA) and propylene glycol (PG) with 6% water appears to decrease the drug permeation. The use of the phospholipid alone without addition of alcohols is also insufficient to achieve the permeation of a saturated solution in water.

EXAMPLE 1

The addition of α-tocopherol or α-tocopherol acetate to the solution of diclofenac sodium as the drug, PL and alcohols leads to an unexpectedly high skin permeation (Table 2). The drug solutions were gelled with polyacrylic acid and triethanolamine in order to form a readily administrable preparation. The skin permeation is only slightly affected by this modification (Table 2).

TABLE 2

| Amounts of diclofenac sodium (μg/2.5 cm$^2$) which diffused in 24 h after addition of PL, α-tocopherol or α-tocopherol acetate and IPA. | |
|---|---|
| 1% Diclofenac NA solution | 1% Diclofenac NA gel |
| 3711 | 3350 |

Figure 2:
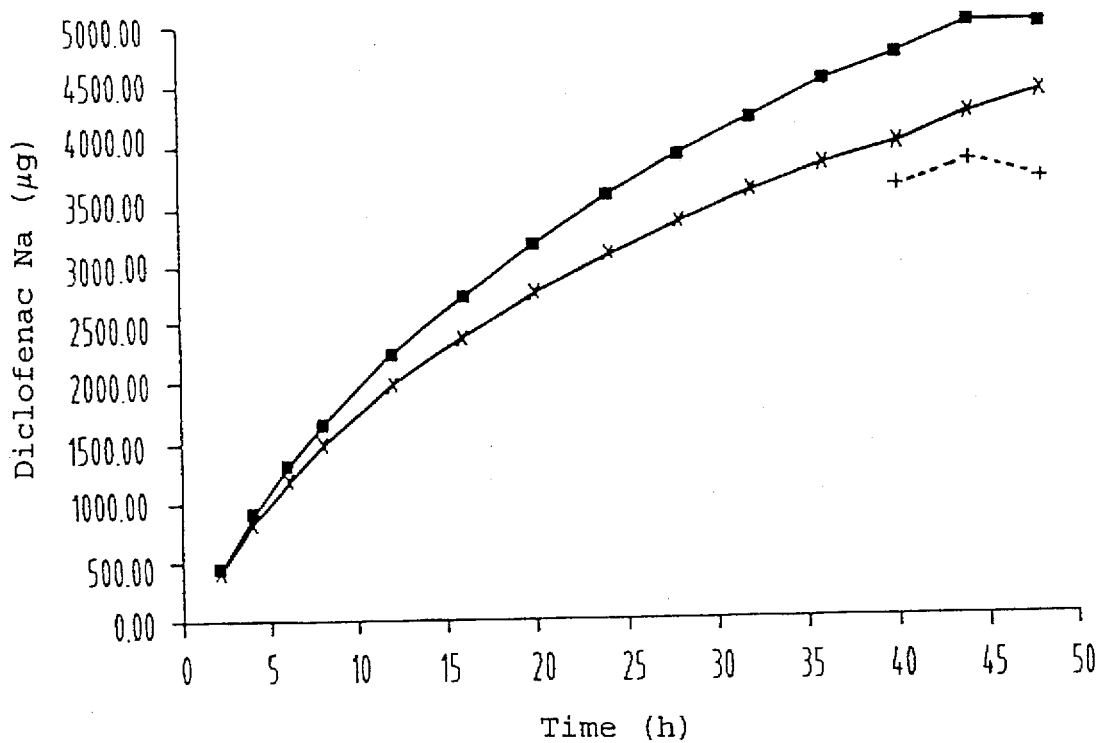
FIG. 2 shows a skin permeation profile in vitro of a diclofenac sodium gel according to the invention.

Both preparations contained identical amounts of PL and IPA. The solution contained 5% d,l-α-tocopherol acetate and the gel 1% d-α-tocopherol. The gel additionally contained 1.5% polyacrylic acid and a sufficient amount of triethanolamine for gelling the polymer. In order to increase the spreading of the gel, a mixture of synthetic oil components was incorporated into the gel. The skin permeation data in vitro of a complete diclofenac Na gel preparation can be seen from FIG. 2.

The flow rate calculated from these data is J=56 μg of drug/cm$^2$/h. It is 1.55 times higher than that of a standard preparation.

Use Example 1

(Diclofenac Na solution)

The following solution can be used as a topical antirheumatic spray:

|  |  |
| --- | --- |
| Diclofenac Na | 1% |
| Phospholipon 80 | 2% |
| d,1-α-Tocopherol acetate | 5% |
| Isopropanol | 20% |
| Water | 72% |

Use Example 2

(Heparin Na gel)

The following gel can be used as a topical antithrombotic preparation:

|  |  |
| --- | --- |
| Heparin Na | 0.5% |
| Phospholipon 80 | 2% |
| d-α-Tocopherol | 1% |
| Polyacrylic acid | 1.5% |
| Triethanolamine | 2.5% |
| Isopropanol | 20% |
| Water | 72.5% |

Use Example 3

(Diclofenac Na gel)

The following gel can be dispersed on the skin very readily. It can be applied to inflamed areas of the body.

|  |  |
| --- | --- |
| Heparin Na | 1% |
| Phospholipon 80 | 2% |
| d-α-Tocopherol | 1% |
| Polyacrylic acid | 1.5% |
| Triethanolamine | 2.5% |

-continued

|  |  |
| --- | --- |
| Decyl oleate | 5% |
| Isopropanol | 20% |
| Water | 67% |

Use Example 4 and Comparison Use Example 1

(Diclofenac Na gels)

Use Example 3 was repeated (Use Example 4). 7.5 g of the 1 per cent diclofenac Na gel were applied in each case to the backs of 12 subjects and washed off after an application period of 6 hours.

For comparison, 7.5 g of a commercially available 1 per cent diclofenac Na gel (Voltaren) were in each case applied to the backs of 12 subjects, the gels again being washed off after an application period of 6 hours.

Figure 3:
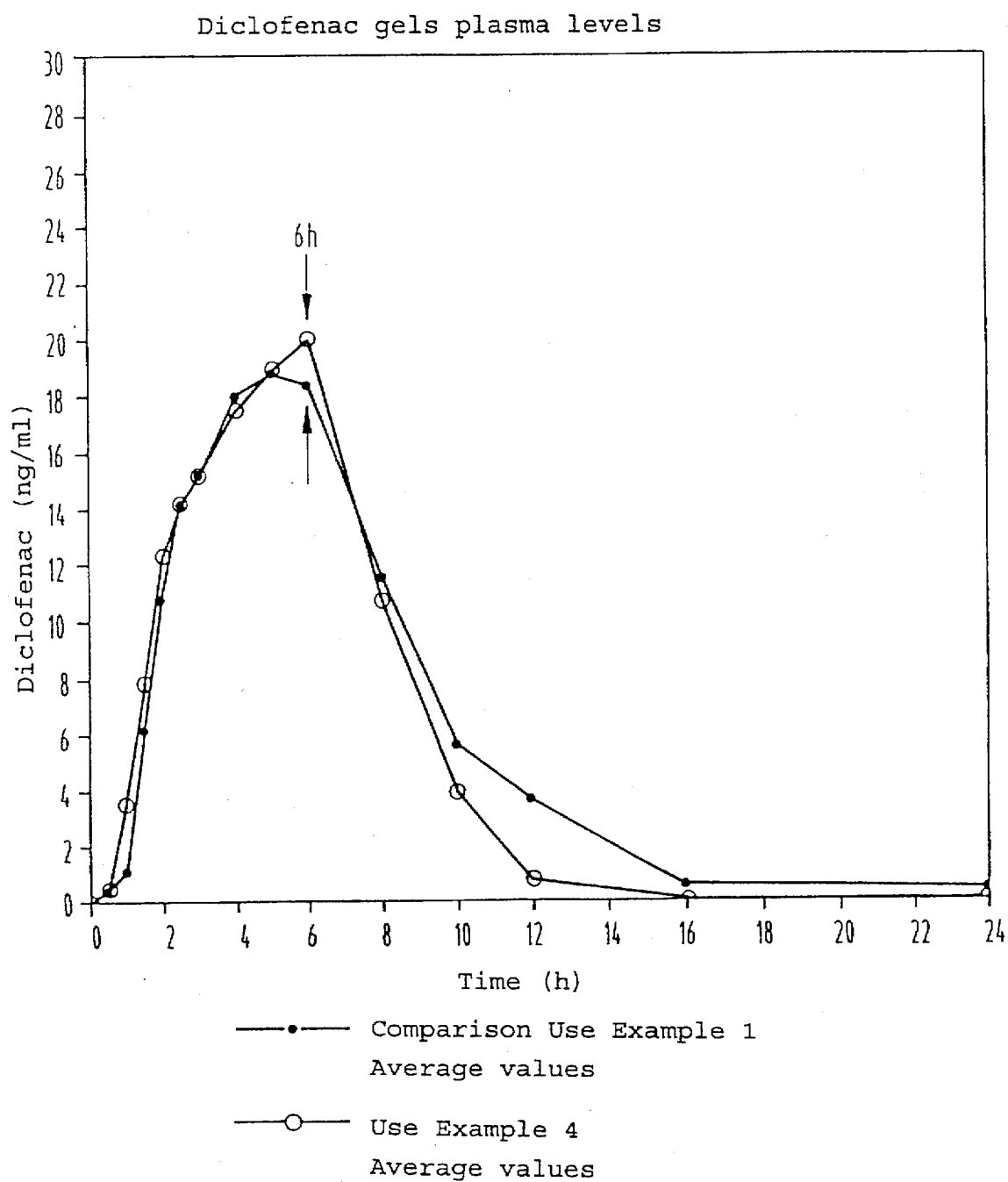
FIG. 3 shows plasma levels as a function of time for a diclofenac Na gel according to the invention and according to the prior art, respectively.

The average values of the plasma levels are shown graphically in FIG. 3. FIG. 3 shows that in Use Example 4 the plasma level was still increasing when the applications were discontinued. In contrast, in Comparison Use Example 1 the plasma level fell even before discontinuing the applications, at an application period of about 5 hours. This fall must be attributed to the fact that the comparison gel does not contain any phospholipid and/or α-tocopherol.

We claim:

1. Drug preparation containing phospholipid, which is a transdermal drug preparation containing water, an aliphatic $C_{1-6}$-alcohol in the range from 1 to 50% (based on the total weight of the preparation), alpha-tocopherol or alpha-tocopherol ester and a hormone, diclofenac Na or heparin Na as the drug.

2. Drug preparation according to claim 1, which contains α-tocopherol or α-tocopherol ester in the range from 0.1 to 10%, based on the total weight of the preparation.

3. Drug preparation according to claim 1 wherein the aliphatic alcohol is an aliphatic $C_2$–$C_4$ alcohol.

4. Drug preparation to claim 1 which contains phospholipid in the range from 0.5 to 20%, based on the total weight of the preparation.

5. Drug preparation according to claim 1 which contains liposomes based on the phospholipid.

6. Drug preparation according to claim 1 which is present as an ointment, gel or spray.

7. Drug preparation according to claim 1, which contains α-tocopherol or an α-tocopherol ester in the range from 0.5 to 7%, based on the total weight of the preparation.

* * * * *

UNITED STATES PATENT AND TRADEMARK OFFICE
CERTIFICATE OF CORRECTION

PATENT NO. : 5,738,869
DATED : April 14, 1998
INVENTOR(S) : Wilfried Fischer et al.

It is certified that error appears in the above-indentified patent and that said Letters Patent is hereby corrected as shown below:

Title Page, Item [73] : change "Haxal AG" to --Hexal AG--.

Signed and Sealed this

First Day of September, 1998

BRUCE LEHMAN

*Attest:*

*Attesting Officer*  *Commissioner of Patents and Trademarks*